United States Patent [19]
Ogasawara et al.

[11] Patent Number: 5,271,821
[45] Date of Patent: Dec. 21, 1993

[54] OXYGEN SENSOR AND METHOD OF PRODUCING THE SAME

[75] Inventors: Takayuki Ogasawara; Fujio Ishiguro; Hiroshi Kurachi, all of Nagoya, Japan

[73] Assignee: NGK Insulators, Ltd., Japan

[21] Appl. No.: 987,051

[22] Filed: Dec. 7, 1992

Related U.S. Application Data

[63] Continuation of Ser. No. 737,797, Jul. 25, 1991, abandoned, which is a continuation of Ser. No. 553,348, Jul. 17, 1990, abandoned, which is a continuation of Ser. No. 316,939, Feb. 28, 1989, abandoned.

[30] Foreign Application Priority Data

| Mar. 3, 1988 | [JP] | Japan | 63-48537 |
| Oct. 12, 1988 | [JP] | Japan | 63-254776 |
| Jan. 20, 1989 | [JP] | Japan | 1-10028 |

[51] Int. Cl.$^5$ ............. G01N 27/56; G01N 27/58
[52] U.S. Cl. ..................... 204/429; 204/428
[58] Field of Search ................... 204/429, 428

[56] References Cited

U.S. PATENT DOCUMENTS

| 4,021,326 | 5/1977 | Pollner et al. | 204/429 |
| 4,080,276 | 3/1978 | Bode | 204/429 |
| 4,164,462 | 8/1979 | Ichikawa et al. | 204/429 |
| 4,177,112 | 12/1979 | Suzuki et al. | 204/153.18 |
| 4,297,192 | 10/1981 | Shinohara et al. | 204/195 S |
| 4,359,374 | 11/1982 | Sano et al. | 204/195 S |
| 4,402,820 | 9/1983 | Sano et al. | 204/425 |
| 4,449,919 | 5/1984 | Takikawa et al. | 431/76 |
| 4,500,412 | 2/1985 | Takahashi et al. | 204/425 |
| 4,584,086 | 4/1986 | Hayakawa et al. | 204/429 |
| 4,626,338 | 12/1986 | Kondo et al. | 204/406 |
| 4,650,697 | 3/1987 | Kitagawa et al. | 427/125 |
| 4,859,307 | 8/1989 | Nishizawa et al. | 204/425 |
| 4,915,814 | 4/1990 | Harada et al. | 204/425 |

FOREIGN PATENT DOCUMENTS

| 57-100343 | 6/1982 | Japan . |
| 60-150450 | 8/1985 | Japan . |
| 61-79155 | 4/1986 | Japan . |

*Primary Examiner*—John Niebling
*Assistant Examiner*—Arun S. Phasge
*Attorney, Agent, or Firm*—Parkhurst, Wendel & Rossi

[57] ABSTRACT

An oxygen sensor having an excellent durability against poisoning by Si is provided by adhering at least one oxide of Mg, Ca, Sr or Ba on the surface or in the pores of the protective layer covering the measuring electrode of the oxygen sensor.

4 Claims, 3 Drawing Sheets

FIG. 9

OXYGEN SENSOR AND METHOD OF PRODUCING THE SAME

This is a continuation of application Ser. No. 07/737,797, filed Jul. 25, 1991, now abandoned, which in turn is a continuation of application Ser. No. 07/553,348 filed Jul. 17, 1990, now abandoned, which in turn is a continuation of application Ser. No. 07/316,939, filed Feb. 28, 1989, now abandoned.

BACKGROUND OF THE INVENTION

1. Field of the Invention

The present invention relates to an oxygen sensor, particularly an oxygen sensor for measuring contents of oxygen contained in gases, such as exhaust gases exited mainly from internal combustion engines, boilers, or the like, and a method of producing the same.

2. Related Art Statement

Heretofore, concentrations of oxygen in exhaust gases exited from internal combustion engines of automobiles, boilers or the like are detected based on the principle of an oxygen concentration cell using oxygen ion conductive solid electrolytes such as zirconia ceramics for controlling an air-fuel ratio or combustion state of such internal combustion engines.

Oxygen sensors of this type of oxygen concentration detector adopt a structure of providing desired electrodes as sensing elements on the inner and outer surfaces of a bottom cylinder or plate shaped solid electrolyte body, exposing the inner electrode to the atmosphere to use it as a reference electrode exposed to a reference gas of a reference oxygen concentration, and exposing the outer electrode to an exhaust gas to be measured to use it as a measuring electrode. By detecting an electromotive force generated by a difference of oxygen concentrations of the reference electrode and the measuring electrode, an oxygen concentration in the exhaust gas is measured.

In conventional oxygen sensors of this type, oxygen sensor elements comprise, as major components, a desired shape of an element body made of a desired oxygen ion conductive solid electrolyte, and a plurality of electrodes arranged on the surface of the element body. Such sensor elements have drawbacks in that the measuring electrode which is the outer electrode is worn and damaged by the action of the exhaust gas of a high temperature to deteriorate its sensing function and cause other problems. Therefore, in order to protect such measuring electrode a porous protective coating layer made of spinel or the like is formed on the measuring electrode to a desired thickness by a plasma thermal spray method or a print sintering method, etc.

However, problems arise even in this sensor element having the protective coating layer. For example, if it is mounted as an oxygen sensor on an exhaust tube of an automobile, and an inferior fuel containing an organic silicon, etc., is used inadvertently or an engine packing or the like containing a silicon compound is used and combusted by the engine, fine particulate shaped or gaseous organic and inorganic silicon compounds are formed and passed through the pores of the protective coating layer to adhere on the surface of the ceramics, or adsorbed on the surface of the measuring electrode or the interface between the measuring electrode and the ceramics to cause deterioration of the sensor output or deterioration of the response, which problems are called silicon poisoning of oxygen sensors.

Meanwhile, prevention of the measuring electrode from reaching the silicon compounds by means of thickening the protective coating or making the pores small is also conceivable. This method prevents fine particles of the silicon compounds from reaching to the measuring electrode. However, the method is not always a satisfactory method since the gaseous silicon compounds can not completely be prevented from reaching the measuring electrode, the initial response is deteriorated due to the thick protective layer and the fine pores, and the fine pores may be become clogged such that the response is deteriorated gradually during the use of the oxygen sensor.

SUMMARY OF THE INVENTION

An object of the present invention is to obviate the above mentioned drawbacks and problems so as to provide an oxygen sensor having a good resistance and endurance to poisoning by the silicon component and a method of preventing the poisoning.

An oxygen sensor which suffers from Si poisoning is easily differentiated from one which does not, because an oxygen sensor which does, mounted on an automobile engine for testing emission values of an exhaust gas, show a larger value of NOx than those one which does not and exceeds a regulation value specified by the government. Therefore, the silicon poisoning may be defined particularly as exceeding a value of NOx caused by exposure of the sensor to the atmosphere of the silicon compounds and measured by an oxygen sensor over the specified regulation value for exhaust gases of automobiles.

The oxygen sensor of the present invention has an oxygen sensor element comprising an oxygen ion conductive solid electrolyte body, a measuring electrode and a reference electrode arranged on the outer and inner surfaces of the oxygen ion conductive solid electrolyte body, a protective layer formed on the measuring electrode, and at least one oxide selected from the group consisting of Mg, Ca, Sr and Ba adhered on the surface or in the pores of the protective layer.

Preferably, the oxygen sensor has aluminum oxide or silicon oxide or an oxide of compounds of Al and Si, such as mullite, etc., adhered on the surface or in the interior pores of the protective layer, in addition to the oxides of Mg, Ca, Sr and Ba.

Preferably, the oxygen sensor has a heating means for heating the sensing portion of the sensor element.

Preferably, the oxygen sensor comprises an oxygen ion conductive solid electrolyte body wound or laminated plates, a reference electrode exposed to a space of a reference gas, and a measuring electrode exposed to a gas to be measured via a porous protective layer arranged on the solid electrolyte, at least the measuring electrode and the porous protective layer being integrally formed by a simultaneous or co-firing, and the porous protective layer having at least one oxide or compound of Mg, Ca, Sr or Ba, adhered on at least the pores of the porous protective layer.

Such an oxygen sensor can be produced by applying or impregnating a solution, suspension or paste of compounds or oxides of Mg, Ca, Sr and Ba on the surface or in the pores of the protective layer, and then heating the layer to yield respective oxides. The other oxides are preferably adhered simultaneously or in advance in the same manner.

Alternatively, the oxygen sensor can be produced by giving Ca, Sr, Ba to the surface or the interior of the protective layer by means of a chemical or physical method, and heating the protective layer to form a respective oxide.

In producing the oxygen sensor, the application of the solution, etc., to the protective layer may be effected by suitably spraying with an air spray gun, dipping or the like.

As the oxygen ion conductive electrolyte material forming the oxygen sensor element body (substrate) for constituting the oxygen sensor, use is made of any publicly known oxygen ion conductive electrolyte. In the present invention, particularly a stabilized zirconia or a partially stabilized zirconia, a desired stabilizer, such as yttria ($Y_2O_3$), calcia (CaO), magnesia (MgO), or itterbia ($Yb_2O_3$), etc, is added to zirconia. Such solid electrolyte material may also be added with a desired sintering additive, e.g., $SiO_2$, $Al_2O_3$, $Fe_2O_3$ or clay, such as kaoline, as is publicly known.

When forming a shaped body having a desired shape of the sensor element body using the materials selected from these solid electrolyte materials, a conventional press forming method, such as a rubber press method can be used, whereby a shaped body is formed which gives the element body a bottomed cylindrical shape or the like which is the main portion of the oxygen sensor element.

Alternatively, the substrate of the plate shaped oxygen sensor element may be formed by preparing a slurry of the solid electrolyte material in 5X-20X by weight of a binder and a solvent, etc., shaping the slurry to a tape shape by means of a doctor blade, etc., and laminating and adhering the tape.

The shaped bodies are then fired to obtain dense ceramics. Thereafter, the shaped bodies are produced into oxygen sensor elements by publicly known methods. For example, the shaped bodies are provided with electrodes and protective coating layers. Alternatively, the shaped bodies are provided with an electrode material which yields the electrode layer after firing on the shaped bodies, and further with a protective layer on the electrode material, and fired to form integral ones.

The raw material of the electrode consists of a platinum group catalytic metal such as platinum, rhodium, palladium, etc., gold, silver, alloys thereof, a cermet of one of the afore-described heat resistant metals and particles of a ceramics (an oxygen ion conductive solid electrolyte is usually used), or the like.

The protective layer is comprised of a plasma thermally sprayed layer of a ceramics, alumina, spinel, or the like, usually being used for the ceramic. In the case when the firing method is adopted to form integral oxygen sensor elements, a printed layer of alumina or an adhered, porous tape-shaped layer of the solid electrolyte may also be used. In this case, the porous tape for forming the protective layer can be formed by the same doctor blade method or the like as described for the substrate made of the solid electrolyte material. Preferably, an organic matter such as carbon or the like which disappears by heating may be added to zirconia, alumina, etc., constituting the protective layer in 10%-40% by weight thereof, to form a protective layer having pores of about 0.1-1 $\mu$m (measured by a pressurized mercury incorporation method) at 40% or more to the entire pores after firing so as to improve both the durability and response of the electrode.

The protective layer preferably has a thickness of 10-500 $\mu$m. If the layer is too thick, the gas permeability in the layer becomes poor and the response of the sensor also becomes poor. Therefore, the porosity of the layer should preferably be properly adjusted to within a range of 5-60%.

The protective layer need not be a single layer, but rather, may consist of plural layers. For example, if the porosity of the plural layers is increased from the electrode side to the surface side, an effect of preventing the clogging of the protective layer can be enhanced. The protective layer is formed integrally by simultaneous firing of ceramic green sheets used for forming the protective layer and the measuring electrode arranged on the solid electrolyte of the substrate. The protective layer formed in this way can carry deposits such as MgO and the like more effectively than the porous protective layer formed by the plasma thermal spray method. Therefore, the protective layer can more effectively prevent poisoning by silicon. This is because the former contained an organic matter, such as carbon, and the like, which disappears during firing such that it can possess a relatively large amount of pores therein after firing and hence carry a larger amount of deposits (such as MgO and the like) than the latter which has relatively small pores and suffers from the clogging of the pores by carrying such deposits.

These protective layers, regardless of whether they were produced by the plasma thermal spray method or the integral firing method, are exposed to a temperature higher than a melting point of the protective layer material or a relatively high temperature such as the sintering temperature. As a result, the outer surface of the layer and the pore surface in the layer through which the gas to be measured penetrates are very low in activity. Namely, they are very stable and are without a gas adsorption function.

Therefore, the gaseous material smoothly reaches the measuring electrode surface and the interface between the electrode and the oxygen ion conductive ceramics (three phase interface) without being adsorbed onto the protective layer. Thus, the oxygen sensor exhibits an output that is dependant upon the $O_2$ partial pressure of the gas to be measured. Meanwhile, among foreign materials exiting automobile engines, burned residue of engine oils, and Pb contained in the gasoline, relatively large particles of oxides, flown onto the surface of the oxygen sensor element, are deposited on the surface and a portion of pores of the protective layer. However, if the porosity and pore diameter distribution of the protective layer are properly adjusted, the deterioration of the response due to clogging, etc., as well as the poisoning of the electrode, can be prevented.

However, organic silicon, such as that contained in crude fuel etc., is combusted or decomposed in cylinders of engines, flown as gaseous silicon compounds and particulate compounds and silica ($SiO_2$) particles to the protective layer surface of the oxygen sensor element, and deposited on the protective layer surface. The gases simultaneously permeate through the protective layer and adhere to the electrode surface and the three phase interface, thus poisoning the electrode.

The inventors have made observations and experiments which lead to a conclusion that, particularly in the case of silicon compounds, deterioration of the characteristic property of the sensor is caused by poisoning of the electrodes, since the deterioration occurs even at a relatively minor amount of deposition of the silicon series particles on the protective layer (deterioration of the response, etc., due to clogging of the protective layer can not be possible at such deposition state). Thus, the poisoning by silicon is a particular problem.

In the most preferable embodiment of the present invention, active particles consisting essentially of magnesia are adhered on the surface or in the pores of the protective layer to effectively prevent the deterioration of the characteristic property of the oxygen sensor caused by the gaseous or ultra fine particulate silicon compounds.

The reason why magnesia in the protective layer is effective is because magnesia catches the active silicon (silicon in the silicon compounds) at the surface thereof to convert the active silicon into the stable silica ($SiO_2$) by the function of the oxygen in the magnesia (MgO), and further into compounds of magnesia and silica. Thus, the silicon is prevented from reaching the surface of the ceramics, the surfaces of the electrodes or the interfaces between the electrode and the ceramics.

Therefore, in order to make the surface of magnesia highly active for the catching, preferable methods or states of adhesion of magnesia are described hereinbelow.

Figure 6:
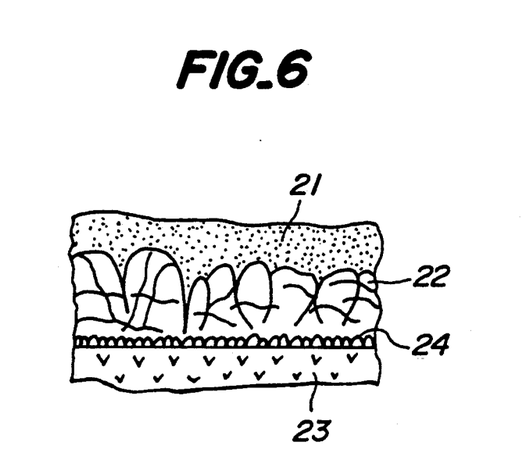
FIGS. 6-9 are, respectively, schematic cross-sectional views of the oxygen sensor element body showing the adhered states of magnesia according to the present invention.

(1) The state of magnesia adhered in layers on the outer surface of the protective layer (FIG. 6).

Powder of magnesia is prepared, dispersed with a binder in an organic solvent or water, adhered on desired portions of the protective layer 22 protecting the electrode 24 at the surface of the solid electrolyte 23 by means of an air gun spray, printing, blushing, dipping of the sensor element, or the like, dried, and fired to form a layer 21 consisting essentially of magnesia.

Instead of the magnesia powder, a powder of magnesium carbonate ($MgCO_3$), magnesium hydroxide or the like, may be used. These powders dissolve slightly, for example, in water, such that they exhibit good adhering properties to the protective layer 22. Preferably, magnesia powder is prepared by grinding coarse particles of molten magnesia to very fine particles so as to obtain an active surface.

The magnesia layer 21 is preferably adhered on the protective layer 22 at a much better gas permeable state than the protective layer 22, considering the response property of the oxygen sensor. For such purpose, an adhesive for magnesia such as an alumina sol, silica sol or the like, may be mixed with magnesia.

If magnesia is fine, the agglomeration function of the fine magnesia may be utilized to keep it in a layered state. Such layers afford an exceedingly improved gas permeability as well as prevent the clogging by sequential catching of the other clogging components in exhaust gases by the surface layer of the layers, and sequential peeling off of the surface layer which has caught such clogging components.

A magnesia layer of a 10–300 $\mu$m in thickness gives a good result. The firing temperature is 1,500° C. or less, preferably 1,000° C. or less. If heat exceeding 1,500° C. is applied the activity of magnesia tends to decrease. Firing at 1,000° C. or less does not influence the activity substantially.

In case of the sensor element wherein the shaped element body, the electrodes, and the protective layer are integrally fired, a good adhesion strength can be exibited if the magnesia layer is also integrally fired.

If metallic magnesium is repeatedly deposited or sputtered on the outer surface of the protective layer and oxidized to yield magnesia, a desired thickness of magnesia layer can be obtained.

Alternatively, a protective layer 22 may again be formed on the layer 21 consisting essentially of magnesia, and the steps may be repeated to obtain a laminate structure of a sandwich of the protective layer and the magnesia layer.

Figure 7:
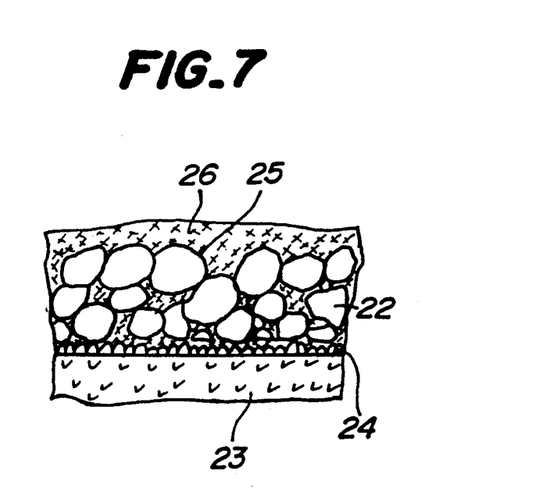

(2) The state of magnesia adhered on the surface and in the pores of the protective layer (FIG. 7).

The protective layer 22 may be impregnated with an organic solvent solution or an aqueous solution of magnesium compound, such as a solution of magnesium chloride, an aqueous hydrochloric acid solution of magnesium hydroxide, or the like, and then heated to 500°–600° C. or higher at which time the respective magnesium salt can decompose, such that fine and active MgO particles 25 are adhered on the protective layer 22. In this case, a relatively small amount of MgO particles exhibits a sufficient effect. Alternatively, a water soluble magnesium salt may once be precipitated as a water insoluble magnesium salt in the protective layer, and then heated up to a desired decomposition temperature or higher to convert the salt into MgO particles. In either case, if the specific surface area of the deposited MgO particles is larger, the effect of preventing the poisoning by silicon becomes larger, so that many fine MgO particles of a diameter of 0.1 $\mu$m or less should preferably exist.

A better effect can be exhibited if the protective layer 22 is preliminarily impregnated, for example, with a solution of an aluminum salt and heated to adhere alumina particles 26 in the protective layer 22, magnesia then being adhered in the aforementioned manners. Instead of alumina particles 26, other particles may also be used, such as particles of silica, spinel, zirconia, etc.

The protective layer 22 preferably has a thickness of 50 $\mu$m or more.

The effect of magnesia is further improved if the protective layer 22 has a coating such that the porosity of the protective layer 22 increases with the distance from the measuring electrode.

The weight ratio of adhered or carried magnesia to the protective layer is 0.05X–60X, preferably 0.5X–20X. The amount of adhered or carried magnesia corresponds to an adhered amount of 0.1–200 mg of magnesia for a sensor element of a publicly known oxygen sensor.

For adjusting the amount of magnesia to be carried by the protective layer, the concentration of the solution may be changed or repetition of impregnation using a solution of a same concentration and firing may be adopted.

Magnesia need not be uniformly distributed throughout the protective layer. The amount of carried magnesia may have a gradient from the measuring electrode to the outer surface exposed to the gas to be measured. In this case, if the carried amount increases to the outer surface, such structure is effective to prevent or mitigate the poisoning. On the contrary, if the carried amount decreases to the outer surface, such structure is effective to prevent or mitigate the clogging.

When the protective layer is formed by the method of laminating the green sheets, magnesia may be incorporated in the protective layer by mixing magnesia, or a magnesium compound which forms magnesia, after firing with the ceramics constituting the protective layer at the time of forming the green sheets. In this case, not all the magnesia is exposed to the pores of the porous protective layer, such that a large amount of magnesia is necessary as compared with the case of carrying magnesia on the layer by the above solution of magnesia after the firing.

Figure 8:
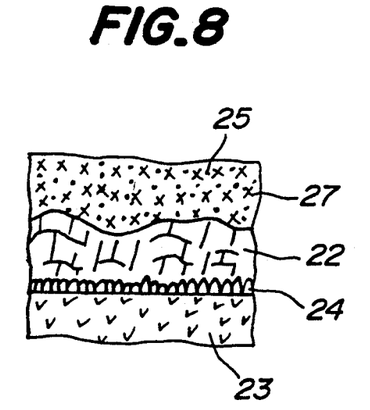

(3) The state of magnesia that is dispersed and adhered in a coating alumina layer (FIG. 8).

Magnesia particles 25 may also be carried on a ceramic particle layer 27 made of porous alumina adhered on the protective layer 22. If a relatively coarse and porous γ-alumina is used as the alumina layer 27 a better result can be obtained.

Instead of alumina, particles of other stable ceramics, such as zirconia, spinel, silica, or the like, may also be used.

Figure 9:
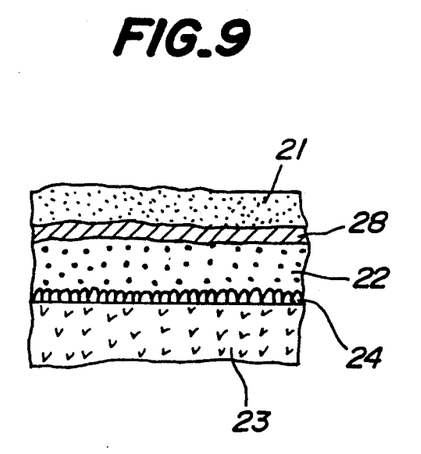

(4) The state of a Pt group metal catalyst adhered on the protective layer (FIG. 9).

A catalyst layer 28 is formed in the protective layer 22 and a layer 21, consisting essentially of magnesia, is adhered on the outer surface of the catalyst layer 28 to improve the durability of the catalyst layer 28.

The catalyst metal 28 may also be adhered in the magnesia layer 21. In this case, the function of magnesia of adsorbing silicon can be improved, so that a better result can be obtained.

(5) The state prepared as an oxygen sensor having a heater.

For enhancing the effect of magnesia, the surface temperature of the sensor is preferably held slightly higher, such that an oxygen sensor having a heater is preferable.

In the case of the oxygen sensor having a heater, the input to the heater can be temporarily increased during use, or if an exhaust gas is to be measured, a high temperature of the exhaust gas is used to hold the temperature of the sensor element up to 850° C. or higher, preferably 900° C. or higher, for 5-30 min so as to restore the characteristic property of the sensor deteriorated by poisoning by silicon. This method is effective when the silicon components are flown in such large amounts that the deterioration of the sensor characteristics can not be prevented by the effect of the magnesia layer alone. This restoring effect is believed to be due to the conversion of the silicon compounds adhered on the electrode surface into stable silica ($SiO_2$) by heating, or the sintering, etc., of the silicon compounds to decrease the surface activity thereof.

BRIEF EXPLANATION OF THE DRAWINGS

For a better understanding of the present invention, reference is made to the accompanied drawings, in which.

NUMBERINGS IN THE DRAWINGS

1 ... bottom cylinder
2 ... reference electrode
3 ... measuring electrode
4 ... protective layer
5 ... oxygen sensor element body
6 ... lower porous protective layer
7 ... upper porous protective layer
8 ... heat-generating portion of heater
9 ... insulation layer
10 ... plate-shaped element body
11 ... housing
12 ... sealing agent
13 ... metal washer
14 ... metal ring
15 ... heater
16 ... metallic cover
17 ... louver
18 ... inlet for exhaust gas
19 ... ceramic
20a ... lead wire
20b ... heat-generating wire
21 ... layer consisting essentially of magnesia
22 ... protective layer
23 ... solid electrolyte
24 ... electrode
25 ... magnesia particles
26 ... alumina
27 ... ceramic particles

DETAILED EXPLANATION OF THE PREFERRED EMBODIMENTS

Referring to FIGS. 1-3a and 3b, the production of the sensor element bodies which are used in the oxygen sensors of the present invention will be explained.

At first, a material for a solid electrolyte composed of 94 mol % of zirconia and 6 mol % of yttria, for example, is added with a small amount of clay as a sintering additive, mixed well, and calcined at 1,000° C. for 3 hrs. The calcined product thus obtained is pulverized in a ball mill of a wet type for 20 hrs. The resultant slurry is added with 1 wt % (relative to solid content) of polyvinyl alcohol as a binder, and granulated by a spray dryer to produce a powder (granulated powder) of the solid electrolyte material of a particle diameter of about 50 μm.

Figure 1:
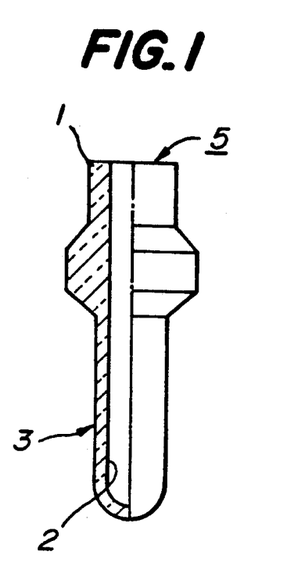
FIG. 1 is a schematic partial cross-sectional view of an example of an oxygen sensor element body which is used in the oxygen sensor of the present invention.

The thus obtained granulated powder of the solid electrolyte material is used for a rubber press forming to produce a bottom cylinder and a plate-shaped sheet. The bottom cylinder 1 is fired, and thereafter provided with a reference electrode 2, a measuring electrode 3, and a protective layer 4 at desired positions so as to produce an oxygen sensor element body 5 of a bottom cylinder shape. In the meantime, the plate-shaped sheet is provided with electrodes 2, 3 and protective layers 6, 7, laminated prior to the firing, and integrally fired to produce a plate-shaped oxygen sensor element body 10.

Figure 2:
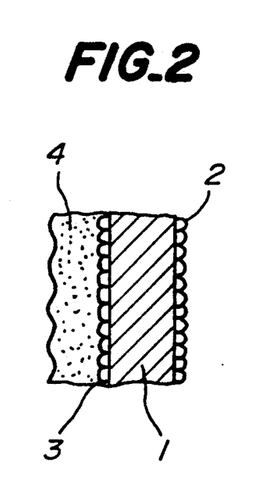
FIG. 2 is a schematic partial cross-sectional view illustrating the details thereof.

Namely, as shown in FIG. 2, which illustrates in enlarged scale the sensing portion of the bottom cylinder shaped oxygen sensor element body 5 of FIG. 1, the bottom cylinder 1, consisting of the oxygen ion conductive solid electrolyte 1, has a porous platinum layer as the reference electrode at the reference gas side, and also a porous platinum layer as the measuring electrode 3 at the side of the gas to be measured. The measuring electrode 3 is coated with a porous protective layer 4 for protection. The porous protective layer 4 is formed by a plasma thermal spray of a spinel powder using a thermal spray gas of Ar/N$_2$. The thickness, porosity and pore diameter of the protective layer 4 are controlled by adjusting the grain size of the spinel powder, and the power of the thermal spray, etc.

Figure 3A:
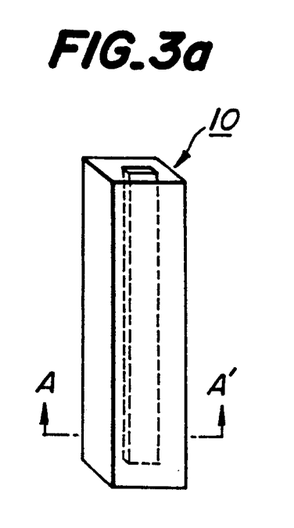
FIGS. 3a and 3b are a schematic perspective view and cross-sectional view, respectively, of another example of the oxygen sensor element body which is used in the oxygen sensor of the present invention.
Figure 3B:
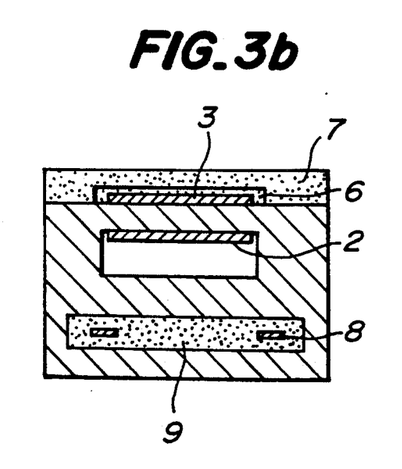

As shown in FIGS. 3a and 3b, the measuring electrode 3 is doubly coated and protected by an underlying porous protective layer 6, consisting of a porous ceramic printed layer, and an upper porous protective layer 7, formed by adhesion of a shaped porous ceramic tape and integral firing thereof. In the embodiment shown in FIG. 3b, the lower protective layer 6 is more dense than the upper protective layer 7, and has a smaller permeability of the gas to be measured than the latter. Also, a heat-generating portion 8 of the heater is integrally incorporated in the plate-shaped sensor element body 10 via an insulation layer 9.

Next, explanations will be made of the assembly and structure of the oxygen sensor using a bottom cylinder shaped oxygen sensor element by referring to FIG. 4. Explanations of a plate-shaped oxygen sensor element such as disclosed in Japanese Patent Application Laid-Open No. 60-150,450 can be used for explaining the plate-shaped oxygen sensor element. Thus, explanations will be omitted and the explanations of 60-150,450 are incorporated herein by reference.

Figure 4:
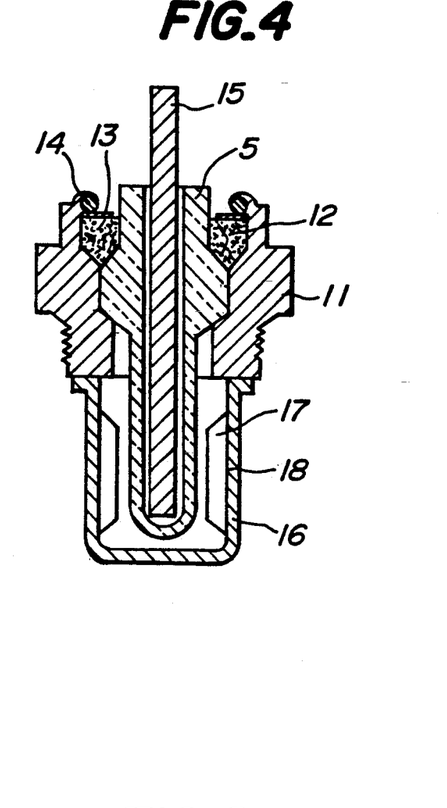
FIG. 4 is a schematic cross-sectional view of an example of the oxygen sensor element which is used in the oxygen sensor of the present invention.

Referring to FIG. 4, the bottom cylinder-shaped oxygen sensor element body 5 is accommodated in a housing 11 and sealed airtightly by a sealing agent 12 made of talc, a metal washer 13, and a metal ring 14, relative to an exhaust gas (not shown) passing through an exhaust gas pipe (not shown). A heater 15 is also accommodated in the cylinder of the oxygen sensor element body 5. A bottomed cylinder-shaped metallic cover 16 is arranged around the outer circumference of the closed end of the oxygen sensor element body 5 for preventing direct impingement of the exhaust gas on the sensing portion of the oxygen sensor element. The upper end of the cover 16 is tightly fixed to the bottom surface of the metallic cover 16. The metallic cover 16 has louvers 17 cut at the side wall of the cover 16 and raised toward the inside of the cover 16, so as to form inlet holes 18 for the exhaust gas.

Figure 5:
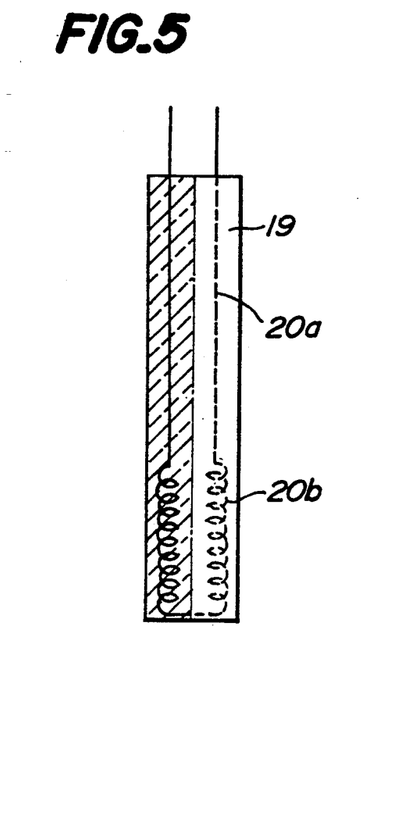
FIG. 5 is a schematic, partial cross-sectional view showing an example of the heater used in the present invention.

As the heater inserted and disposed in the cylinder of the oxygen sensor element body 5 as shown in FIG. 4, use is made of, for example, a ceramic heater composed of a ceramic 19 made of alumina, and a lead wire 20a and a heating wire 20b such as tungsten wire embedded in the ceramic 19, as shown in FIG. 5.

PREFERRED EMBODIMENTS OF THE INVENTION

Hereinafter, the present invention will be explained in more detail with reference to examples.

Example 1

The following oxygen sensor elements ①-⑦ are prepared and assembled into oxygen sensors for testing the durability of the characteristic properties of the oxygen sensors.

① A magnesia powder of an average particle diameter of 0.7 μm is added with a binder, a dispersant, and an organic solvent to form a paste. The paste is printed on the porous protective layer of the plate-shaped oxygen sensor element of FIG. 3, dried at 120° C. for 30 min, and fired at 600° C. in air for 1 hr. The magnesia layer thus produced has an average thickness of 30 μm.

② A magnesia powder of an average particle diameter of 0.3 μm is slowly stirred and dispersed in water added with a binder. The slurry the sensor element of FIG. 1 is put in the slurry until the measuring electrode is immersed, pulled up, and dried. The procedure is repeated three times. Thereafter, the sensor element is fired at 800° C. in air for 30 min. The magnesia layer thus produced has an average thickness of 50 μm.

③ Magnesium hydroxide is dissolved in a dilute aqueous solution of hydrochloric acid at room temperature to prepare a saturated solution. The sensing portion of the plate-shaped sensor element of FIG. 3 is immersed in the solution, then subjected to 600° C. in air for 1 hr to adhere magnesia on the surface and in the pores of the protective layer.

④ A powder of porous γ alumina of an average particle diameter of 3.7 μm is added with an alumina sol and water to form a solution. The sensor element of FIG. 1 is immersed in the solution, and fired at 500° C. Then, the sensor element is immersed in the saturated solution described in ③, and fired at 600° C. in air for 1 hr.

⑤ On the coating of the sensing portion of the plate-shaped sensor element of FIG. 3 is formed a catalyst containing porous alumina layer composed of alumina, platinum and rhodium in a weight ratio of 10:1:0.1, to a thickness of 10 μm.

Meanwhile, a magnesia powder of an average particle diameter of 3 μm is added with an alumina sol in such an amount that it occupies 5 wt % of the total weight to prepare a suspension.

The above plate-shaped sensor element is immersed in the suspension to form a magnesia layer of an average thickness of 25 μm.

⑥ The procedure of ② is repeated to form a magnesia layer of an average thickness of 150 μm.

⑦ The procedure of ② is repeated, except that a silica powder of an average particle diameter of 1.3 μm is added in an amount of 12 wt % relative to the magnesia powder.

As described above, oxygen sensor elements ①-⑦ are produced and subjected to durability tests using engine benches. In the durability test, a four cylindered 1.5 l gasoline engine having an electronic gasoline injector (EGI) is used, and an operation condition is selected wherein the exhaust gas temperature varies at a cycle of 30 min in a range of 400°-700° C. Organic silicon (b.p. about 80° C.) is added in a gasoline for the test such that the gasoline contains 0.03 g of Si per 1 liter.

A λ characteristic property and response time ($T_{RL}$) of the sensor elements are measured before the durability test and after the durability test of 10 hrs.

The λ characteristic property is determined by changing the λ value of the exhaust gas of the above engine to 0.95-1.05 by a signal from the exterior, and measuring the λ value when the sensor output becomes 0.4 V. The λ value of the exhaust gas is measured by a gas analyzer. The temperature of the exhaust gas is controlled to 350° C.±10° C.

Response time ($T_{RL}$) is determined by changing the λ value of the same engine from 0.95 to 1.05, and measuring a time required for the decrease of the sensor output to 0.4 V. The result is expressed as $\Delta T_{RL}(=T_{RL}$ of after the durability test$-T_{RL}$ of before the durability test). Samples are three in number for each condition. Test Nos. 1, 4, 6, 8, 9, 11, 13 and 15 are effected at a constant heater heating voltage of D.C. 13 V. Test Nos. 2, 5 and 12 are effected by controlling a heater heating voltage to respective sensor element temperature as shown in the following Table 1. In the measurements of λ values and $\Delta T_{RL}$, those values which necessitate heating by the heater are all measured at a sensor input of D.C. 13 V. Sensor temperature is the highest temperature of the sensor element during the durability test and is at the outer surface of the sensor element by an R thermocouple of wires of a diameter of 0.2 mm. The results are shown in Table 1.

TABLE 1

| Test No. | Sensor element | Heater heating in durability test | λ value (0.4 V, 350° C.) Before durability test | λ value (0.4 V, 350° C.) After durability test | $\Delta T_{RL}$ (350° C.) msec |
|---|---|---|---|---|---|
| Example 1 | ① | Yes (max 710° C.) | 1.003 | 1.013 | 40 |
| 2 | ① | Yes (max 850° C.) | 1.004 | 1.008 | 20 |
| 3 | ② | No | 1.008 | 1.027 | 70 |
| 4 | ② | Yes (max 770° C.) | 1.003 | 1.009 | 30 |
| 5 | ② | Yes (max 860° C.) | 1.002 | 1.006 | 20 |
| 6 | ③ | Yes (max 750° C.) | 1.002 | 1.009 | 30 |
| 7 | ④ | No | 1.006 | 1.020 | 60 |
| 8 | ④ | Yes (max 760° C.) | 1.001 | 1.009 | 30 |
| 9 | ⑤ | Yes (max 730° C.) | 1.002 | 1.012 | 40 |
| 10 | ⑥ | No | 1.007 | 1.022 | 50 |
| 11 | ⑥ | Yes (max 790° C.) | 0.998 | 1.003 | 30 |
| 12 | ⑦ | Yes (max 900° C.) | 1.001 | 1.004 | 10 |
| Comparative Example 13 | Plate shaped sensor | Yes (max 740° C.) | 1.002 | 1.045 | ≧1 sec |
| 14 | Cylindrical sensor | No | 1.010 | ≧1.05 | unmeasurable |
| 15 | Cylindrical sensor | Yes (max 760° C.) | 1.002 | 1.050 | unmeasurable |

From the results of the above Table 1, all the oxygen sensors of the present invention exhibit splendid durability as compared with those of the Comparative Examples.

Example 2

The plate-shaped oxygen sensor elements of FIG. 3 are immersed at the sensing portions in a saturated aqueous solution of a respective nitrate of Mg, Ca, Sr or Ba or a mixed solution of Mg and Ca, then fired at 900° C. in air for 1 hr to prepare 5 types of sensor elements each having adhered MgO, CaO, SrO or BaO or a composite of MgO and CaO on the surfaces and in the pores of the protective layer and the measuring electrode. The sensor elements are assembled into oxygen sensors as shown in FIG. 4.

The five types of oxygen sensors and a reference oxygen sensor not subjected to the specific treatment as in the present invention, are tested in the durability test using an engine bench. In the durability test, a four cylindered 1.5 l gasoline engine having EGI is used, the exhaust gas temperature is held constant at substantially 500° C., organic silicon is added to a gasoline for the test such that the gasoline contains about 0.02 g of Si per 1 liter, and the durability test duration is 20 hrs.

The results are shown in the following Table 2.

The λ characteristic property and response time ($T_{RL}$) are measured in the same way as in Example 1.

TABLE 2

| | Sample No. | Adhered by | Heating of the heater during durability test | λ value (0.4 V, 350° C.) Before durability test | λ value (0.4 V, 350° C.) After durability test | $\Delta T_{RL}$ (350° C.) msec |
|---|---|---|---|---|---|---|
| Invention | 1 | MgO | Yes | 0.998 | 0.999 | 20 |
| | 2 | CaO | Yes | 0.999 | 1.002 | 30 |
| | 3 | SrO | Yes | 0.998 | 1.003 | 20 |
| | 4 | BaO | Yes | 1.000 | 1.005 | 10 |
| Comp. Ex. | 5 | Composition of MgO CaO | Yes | 0.998 | 0.999 | 20 |
| | 6 | None | Yes | 1.002 | 1.015 | 80 |

As seen clearly from the above Table 2, the oxygen sensors of the present invention having an adhered oxide of Ca, Sr, or Ba, or an adhered composite of MgO and CaO, exhibit good results similar to the oxygen sensor having the oxide of Mg as compared with the oxygen sensor of the Comparative Example, against the poisoning by silicon. The oxygen sensor having the adhered oxide of Mg gave the smallest change of λ value, showing the best result against the poisoning by silicon.

As is apparent from the above detailed explanations, the oxygen sensor of the present invention and the method of producing the same can prevent the deterioration of the characteristic properties of oxygen sensors caused by gaseous or ultra-fine particulate-shaped silicon compounds, by virtue of adhering at least one oxide selected from the group consisting of oxides of Mg, Ca, Sr, Ba, or mixtures thereof, on the surface or in the pores of the protective layer. Also, the method is a simple and easy way of adhering at least one oxide of Mg, Ca, Sr, Ba, or mixtures thereof, on the protective layer or in the protective layer. Thus, the method is economical and easy for production.

Although the present invention has been explained with specific examples and numerical values, it is of course apparent to those skilled in the art that various changes and modifications thereof are possible without departing from the board spirit and aspect of the present invention as defined in the appended claims.

What is claimed is:
1. An oxygen sensor element, comprising:
an oxygen ion conductive solid electrolyte body;

a reference electrode and a measuring electrode disposed on said solid electrolyte body;

a porous ceramic protective layer formed on said measuring electrode; and conversion means for converting active silicon to stable silica or compounds thereof, said conversion means comprising a catalytically active layer of particles consisting essentially of MgO, said catalytically active layer being adhered on the surface of the porous protective layer.

2. The oxygen sensor of claim 1, wherein said oxygen sensor element further comprises a heater for heating said solid electrolyte body.

3. An oxygen sensor comprising:

an oxygen ion conductive solid electrolyte body;

a reference electrode exposed to a reference gas;

a measuring electrode arranged on the solid electrolyte body and exposed to a gas to be measured;

a porous ceramic protective layer arranged on the measuring electrode, the measuring electrode and the porous ceramic protective layer being integrally formed by a simultaneous firing, said porous protective layer consisting of a ceramic material; and conversion means for converting active silicon to stable silica or compounds thereof, said conversion means comprising a catalytically layer of particles consisting essentially of MgO, said catalytically active layer being adhered on the surface of the porous protective layer.

4. The oxygen sensor of claim 1, further comprising alumina, silica, spinel, mullite or zirconia adhered on the surface of said protective layer.

* * * * *